United States Patent [19]

Takács et al.

[11] 4,107,851
[45] Aug. 22, 1978

[54] METHOD OF AND APPARATUS FOR FLUIDIZATION

[75] Inventors: István Takács; György Fábry; László Pap; Gyorgy Kiszely, all of Budapest, Hungary

[73] Assignee: Richter Gedeon Vegyeszeti Gyar Rt., Budapest, Hungary

[21] Appl. No.: 746,671

[22] Filed: Dec. 2, 1976

[30] Foreign Application Priority Data

Dec. 9, 1975 [HU] Hungary .................. RI 582

[51] Int. Cl.² .............. F26B 3/08; F27B 15/00
[52] U.S. Cl. ...................... 34/10; 34/57 A; 432/15; 432/58
[58] Field of Search .............. 34/10, 57 A, 57 R; 432/15, 58; 266/172

[56] References Cited

U.S. PATENT DOCUMENTS

| | | | |
|---|---|---|---|
| 2,750,681 | 6/1956 | Berry | 34/57 A |
| 2,813,351 | 11/1957 | Godel | 34/10 |
| 3,079,222 | 2/1963 | Reeve | 34/10 |
| 3,281,508 | 10/1966 | Goulounes | 432/15 |
| 3,861,058 | 1/1975 | Whelan | 34/10 X |

*Primary Examiner*—John J. Camby
*Attorney, Agent, or Firm*—Young & Thompson

[57] ABSTRACT

A fluid is introduced into a bed of a material to be fluidized along the bottom surface thereof at a pulsating velocity which is by an order of magnitude greater than the velocity of fluidization.

Such method can be carried out in a fluidization apparatus having a per se known distributor the orifices of which are overlapped by reeds which vibrate when a pressure fluid is introduced into a bed above the distributor.

10 Claims, 9 Drawing Figures

METHOD OF AND APPARATUS FOR FLUIDIZATION

BACKGROUND OF THE INVENTION

This invention relates to a method of and apparatus for fluidization and more particularly for drying bulk material.

Fluidization is employed extensively for contacting gaseous materials with solids since contacting takes place on relatively much larger surfaces when contacted solids are fluidized. Fluidization is employed for conveying purposes as well because in their fluidized state solids behave as liquids and, thus, can more easily be advanced.

Fluidization is generally obtained by having a bed of the material to be fluidized traversed by a fluidizing gaseous medium or fluid. However, various difficulties may be met with in the course of fluidization. Gas velocities needed for obtaining and maintaining fluidization are difficult to conform to values required for technological reasons as in case of drying, absorbing, chemical reactions, conveying and the like. Powder-like or minute particles of fluidized solids may deposit or flow back into inlet areas of fluidizing fluids at shut down periods and cause start-up problems. Channels may be formed in fluidized beds particles of which may be transported in the stream of withdrawing fluidizing fluids. Fluidized beds may have uneven surfaces and variable porosities both of which have adverse effects on start-ups. Homogeneous gas distribution in fluidized beds could only be obtained with beds of limited breadths.

Such difficulties could partly be overcome by fluidization methods where a fluidizing fluid of pulsating flow velocity is employed and is introduced at a plurality of level locations simultaneously. The fluidizing fluid enters through tuyeres in orifices of a distributor wherefrom it withdraws substantially transversely of the bed.

The present invention is thought to be an improvement over such methods in that a more uniform fluidization is permitted and, thereby, considerably broader beds are rendered possible without backflowing at shutdowns and start-up problems at refluidizations.

SUMMARY OF THE INVENTION

The invention relates to an improved method of fluidization and more particularly of drying bulk material. A fluidizing fluid is introduced at the bottom of a bed to be fluidized at a velocity which is by at least one order of magnitude greater than the velocity of fluidization. The flow direction of the fluidizing fluid which issues from the orifices of a distributor is parallel to the bottom of the bed. It has been found that such inflow direction and velocity in connection with the pulsation of the latter and the employment of a plurality of level inlets results in vigorous circulating currents or fluxes throughout the bed by which the entire material of the later is set into uniform bubbling motion. Thus, a homogeneous loose bed can be obtained in an unusually broad band of velocities. In addition, no particles will deposit in the inlets of the fluidizing fluid since they would be unable to proceed against a horizontal flow of high speed gaseous medium.

The flow velocity of the fluidizing fluid will preferably be pulsated by permitting a resilient variation of its inflow cross-sectional areas. Such resilient variation results in an automatic interdependence between flow velocity and penetration depth of a fluid jet so that flow velocities can be selected at which circulating fluxes die just at the surface of the bed. This means that the whole mass of the bed is bubbling, yet no particles are transported in the stream of the fluid.

Fluidization in the above described manner will preferably be carried out by apparatus of the type having a first passage which serves for receiving the material to be fluidized in the form of a bed. A second passage is separated from the first passage by a distributor and is destined to conduct a fluidizing fluid to the aforesaid distributor. Rows of orifices in the distributor permit the fluid to penetrate into the bed.

The present invention suggests to improve such known apparatus by providing reeds on the outlet sides of the orifices in the distributor. Reeds having the nature of resilient tongues located above the orifices are liable to be raised by the inflowing fluid and then snap back into their rest positions. Thereby, the reeds abruptly and periodically interrupt the fluid flow through the respective orifices. Thus, a pulsating flow velocity is automatically obtained. Obviously, in their rest positions each reed has to overlap its associated orifice so that no particles of the bed may have access to the passage beneath the distributor.

Oscillation frequencies and amplitudes of the reed movements are determined by the material and sizes of the reed as well as by the flow velocity of the fluid, and the consistency and thickness of the bed.

Automatic oscillation of the reeds permits working with beds which are composed of grains of different sizes or of sticky materials.

BRIEF DESCRIPTION OF THE DRAWINGS

Similar details are referred to by same reference numerals throughout the drawings.

DESCRIPTION OF THE PREFERRED EMBODIMENTS

Figure 1:
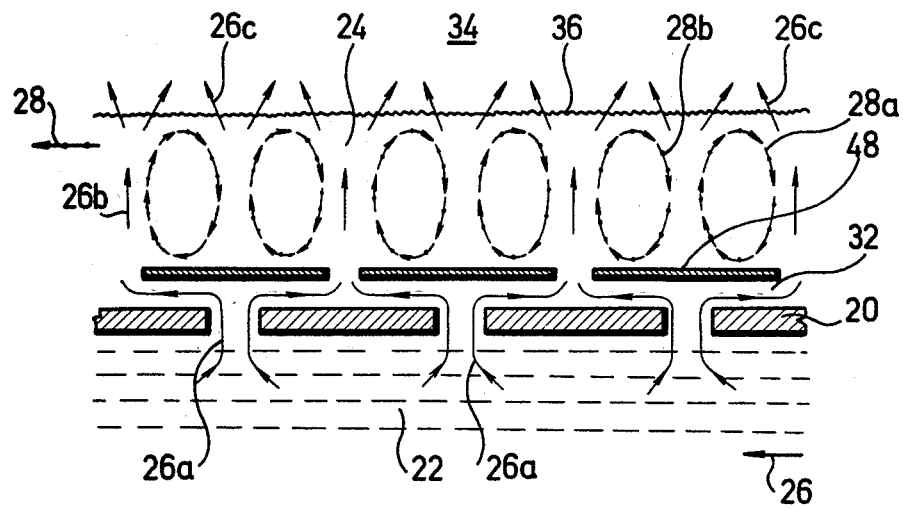
FIG. 1 shows the essence of the invention by means of a schematic representation of streams and fluxes in a longitudinal sectional view of a distributor.

FIG. 1 illustrates the working principle of the invention.

Reference character 20 designates a distributor which, as is known, serves for introducing a gaseous fluidising fluid 22 to a bed 24 of solid material to be fluidized. While the flow direction of the fluid 22 is indicated by continuous arrows 26, dotted arrows 28 suggest movements of the bed material. Orifices in the distributor 20 known per se are referred to by reference numeral 30.

The present invention provides resilient transverse passageways 32 above each orifice 30 which deflect the fluid flow in a direction parallel to the bottom surface of the bed 24 as suggested by arrows 26a. Resiliency of the passageways 32 means that their cross-sectional flow areas vary under mutual influence of various factors such as flow velocity, bed thickness and consistency, nature and size of constructional material etc. as will be more apparent hereinafter in the course of detailed description.

As the fluid 22, through an orifice 30, enters a passageway 32 its pressure causes an expansion of the latter with consequent changes of gas pressure and velocity. As the gas pressure decreases, the resilient passageway 32 resumes its initial position whereupon the whole cycle starts anew. Thus, the resilient passageways 32 periodically vary their cross-sectional areas and, thereby, render the flow velocity of the fluid automatically pulsating.

Jets of the fluid 22 leaving the passageways 32 along the bottom of the bed 24 meet each other and become mutually deflected in the direction of arrows 26b upwardly so that they penetrate into and through the bed 24. Bed particles are thereby seized by the initial strong jets and carried upwards. As flow velocity decreases due to spreading of the fluid in the bed, upwardly travelling bed particles lose their upward momentum and, by gravity, begin to descend substantially in regions above the orifices 30. Thus, the whole mass of the bed 24 is set into motion while flow velocity of the fluid 22 is slowed down to a value at which it leaves the bed 24 in the direction of arrows 26c into an ambiency 34 without carrying away any bed particles so that a quiet and even bed surface is obtained.

The above described fluid supply results, as it seems, in forming circulating fluxes of pairwise opposite rotational directions indicated by dotted arrows 28a and 28b which set the whole bed material into vigorous bubbling and, thus, into a well fluidized state.

Figure 2:
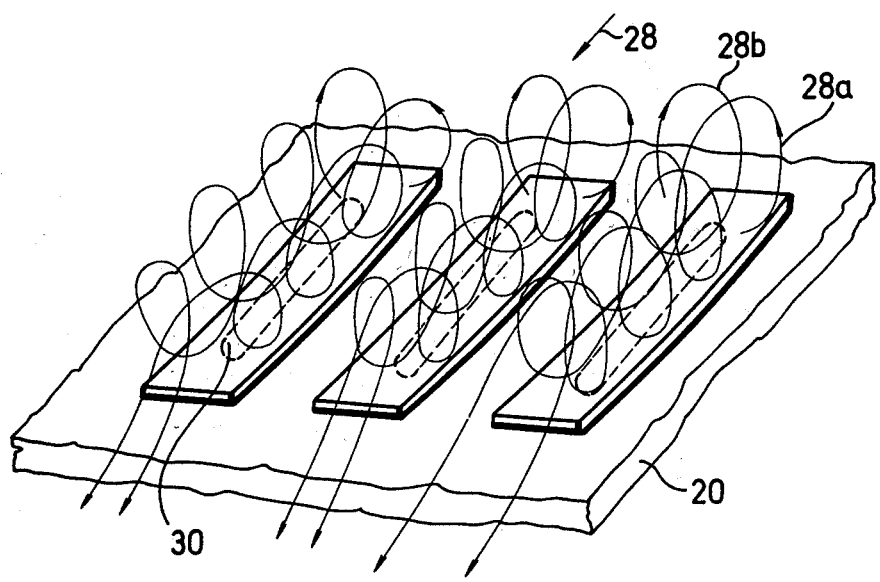
FIG. 2 is a perspective schematic view of a detail of a distributor with a fluidized material flowing on it.
Figure 3:
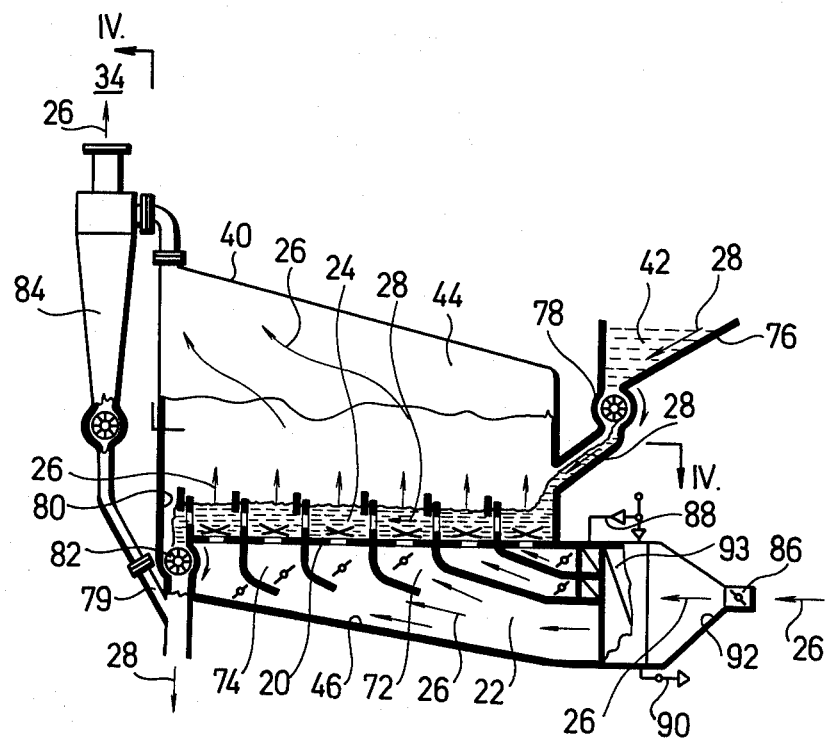
FIG. 3 illustrates a longitudinal sectional view of one embodiment of an apparatus according to the invention taken along the line III — III of FIG. 4.

Although such method may be used for fluidizing stationary beds it is particularly suitable for continuous operation. This will now be described by reference to FIG. 2.

With continuous operation, material to be fluidized is constantly supplied onto a distributor 20, and fluidized material is constantly withdrawn therefrom as will hereinafter be described in greater detail. Due to such material supply and withdrawal the bed proceeds on the distributor from an inlet towards an outlet as indicated by arrow 28. Meanwhile, circulating fluxes 28a and 28b described above are formed which, in the course of proceeding, become sort of helicoids. Thus, it will be a suitably fluidized bubbling mass which arrives at the outlet referred to above. As far as orifices 30 with resilient passageways 32 are provided, the bed 24 will be exempt of quiescent areas so that a very efficient fluidization will be obtained along the whole perforated distributor surface the width of which is thus practically unlimited.

The method according to the invention may, e.g., in case of drying, be carried out in an apparatus shown, by way of example, in FIGS. 3 to 7.

The interior of a casing 40 is subdivided by a distributor 20 into a passage 44 for receiving a bed 24 consisting of wet solid material 42 to be dried, and into a passage 46 for conducting a gaseous medium such as fluid 22 for introducing it by means of the distributor 20 into the bed 24.

Figure 5:
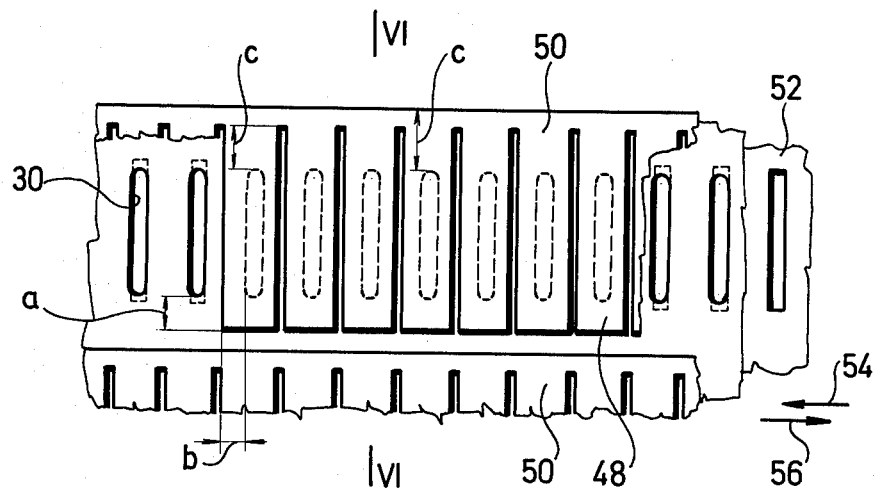
FIG. 5 shows a plan view of a detail of FIGS. 3 and 4 on a relatively larger scale.
Figures 6, 8:
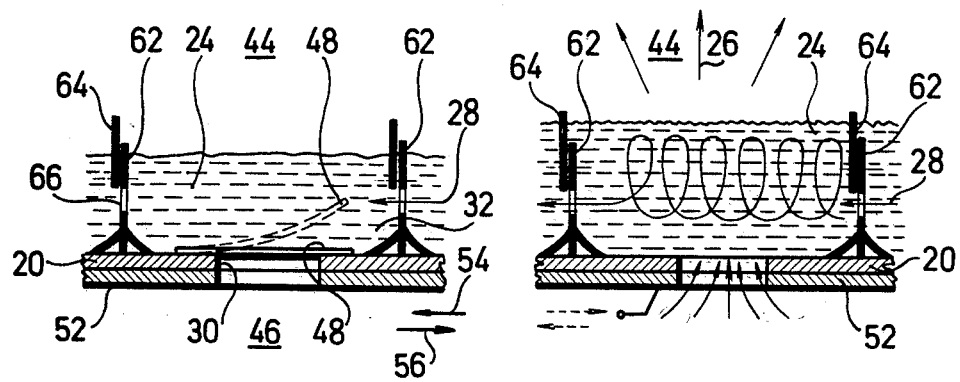
FIG. 6 represents a cross-sectional view taken along the line VI — VI in FIG. 5.
FIG. 8 is a cross-sectional view taken along the line VIII — VIII of FIG. 7.

Details of the distributor 20 are shown in FIGS. 5 and 6. In the instant case, the orifices 30 interconnecting the passages 44 and 46 constitute longitudinal slits which lie parallel to the flow direction 28 of the bed 24. On the upper side of the distributor 20 facing the passage 44 the orifices 30 are overlapped each by a reed 48. Overlapping is referred to by reference characters a, b, and c, in FIG. 5. In the represented embodiment, the reeds 48 are formed by teeth 50 of a metal plate incised in the manner of a rake. Such expedient is preferable from a plurality of points of view such as simple manufacture, reliable overlapping and the forming of slits of small resistance and considerable specific circumference (circumference versus surface area).

Likewise, in the instant case, on its lower side facing the passage 46 the distributor 20 is provided with a lock plate 52 arranged for adjusting the cross-sectional flow area of the orifices 30. Thereby, the operation of the apparatus may be adapted to operational conditions of drying since higher moisture contents require relatively more air while in case of materials of lower moisture content less air will be needed to obtain a certain degree of dryness. Adjustments may be effected also during operation by displacing the lock plate 52 in one of the directions designated by arrows 54 and 56. Thereby, efficiency may greatly be enhanced. The lock plate 52 is guided either on the distributor 20, or on side walls 58 and 60 of the casing 40 in a manner known per se, e.g., by slide rails which are, for the sake of clarity, not represented in the drawing.

In the instant case, on its upper side the distributor 20 carries sluices 62 arranged transversely as regards the flow direction 28 of the bed 24. Height of the slucies 62 may be adjusted by means of sluice valves 64 in a manner known per se. Such arrangement permits simple flow control and prevention of back flows.

As illustrated, the sluices 62 may comprise orifices 66 the cross-sectional flow area of which can likewise be adjusted by the sluice valves 64. Such expedient permits adjusting the flow rate without altering the thickness of the bed 24. Larger particles at the bottom of the bed are permitted to proceed as well. Thereby, any tendencies to segregation may be obviated which is very important in case of continuous operation as will be clear to any skilled art worker.

Figure 4:
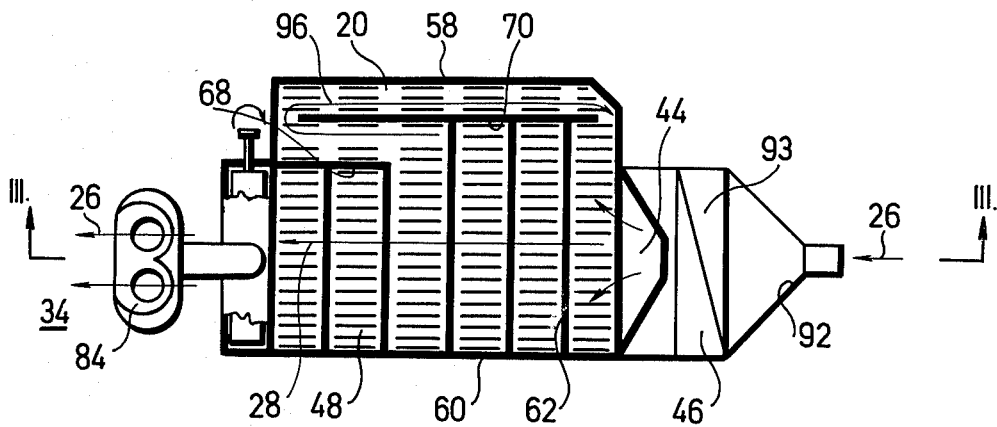
FIG. 4 is a longitudinal sectional view taken along the line IV — IV of FIG. 3.

With the represented embodiment, the sluices 62 are arranged on the distributor 20 so that they pairwise enclose a row of orifices 30 as can be seen particularly in FIG. 4. The sluices 62 extend to longitudinally arranged baffle plates 68 and 70 which are shorter than the passage 44 and serve to recirculate a portion of the bed material to the inlet extremity of the distributor 20, the flow path of which is extended thereby. By such recirculation even substances difficult to fluidize can be rendered accessible to fluidization. For instance, particles of granular metals may be coated with a paste which helps to fluidize such materials.

The lower side facing the fluid passage 46 of the distributor 20 is provided with conditioning compartments 72 arranged one behind the other as regards the flow direction 26 of the fluid 22. The compartments 72 comprise, in the instant case, each a throttle valve 74 which permit an adjustment of their cross-sectional flow area. Furthermore, the compartments 72 register each with a row of orifices 30 between a pair of sluices 62 although other arrangements might be selected as well, if necessary.

The employment of compartments 72 as described above furthers adaptation of operational conditions to requirements of drying since each compartment 72 may have different thermal and/or humidity conditions established therein.

A chute 76 serves for supplying wet material 42 to be dried onto the distributor 20 at one of its extremities and comprises an inlet thereto. A feed rotor 78 ensures uniformity of supply as is known per se.

A discharge shaft 80 constituting an outlet is provided at the other extremity of the distributor 20 and is provided with a feed rotor 82 which ensures a uniform discharge likewise in a manner known per se.

The passage 44 itself opens into a vortex chamber or cyclone 84 which, in turn, opens into the ambiency 34. At its lower extremity the cyclone 84 is connected with the discharge shaft 80.

Reference numeral 86 designates a gate by which inflow cross-sectional areas of the fluid 22 may be adjusted according to operational requirements. Steam may be supplied to the system at 88. Precipitations or deposits may be discharged at 90. Reference numeral 92 designates a distribution hopper while reference numeral 93 refers to a steam calorifer connected with the steam supply means 88.

In operation, wet solid material 42 to be dried is supplied through the chute 76 by means of feed roller 78 onto the distributor 20 as indicated by arrow 28. At the same time, air will be introduced through gate 86 into distribution hopper 92 as indicated by arrows 26 wherefrom it flows into the passage 46 and through the compartments 72 into orifices 30 of the distributor 20.

In each compartment 72 there prevail individually selected temperature and/or moisture conditions so that the air jets entering the passage 44 through the orifices 30 are conditioned in accordance with the temperature and/or moisture conditions prevailing between the sluices 62.

More particularly, the air as fluidizing fluid 22 flows from compartments 72 into orifices 30 of the distributor 20 and raises the reeds 48 from under which it penetrates into the bed 24 as indicated by arrows 26a (FIG. 1). Raising of the reeds 48 creates resilient passageways 32 by which the inflowing air is caused to discharge along the bottom side of the bed 24 as has been explained in connection with FIG. 1. Meanwhile the flow velocity of air suddenly increases while decreasing pressure permits the reeds 48 to resume their initial position where they overlap their associated orifices 30 as shown in FIG. 5 at a, b and c.

Closed reeds 48 are again exposed to the pressure of the inflowing fluid 22 so that they rise anew and the whole cycle of reed movements and air flow is started again. This is the way in which the reeds 48 carry out vibrational motions and thereby automatically ensure the building up of circulating fluxes and bubbling as has been described in detail in connection with FIGS. 1 and 2. It means that a flow pattern as shown in FIG. 1 will appear between each pair of sluices 62 as indicated by arrows 26b and 28b in FIGS. 1 and 2, respectively.

The air leaves the bed 24 in the direction of arrows 26c after having been in close contact with particles of the fluidized wet solid material 42 and having taken over their moisture content to a desired degree. The wet air flows into the cyclone 84 where transported solid particles will precipitate so that it will be pure air which leaves the cyclone 84 into the ambiency 34. Precipitated solid particles drop from the cylone 84 into discharge shaft 80 wherefrom they leave together with dry solid material 79 in the direction of dotted arrow 28 in a manner known per se to a place of processing.

Figure 7:
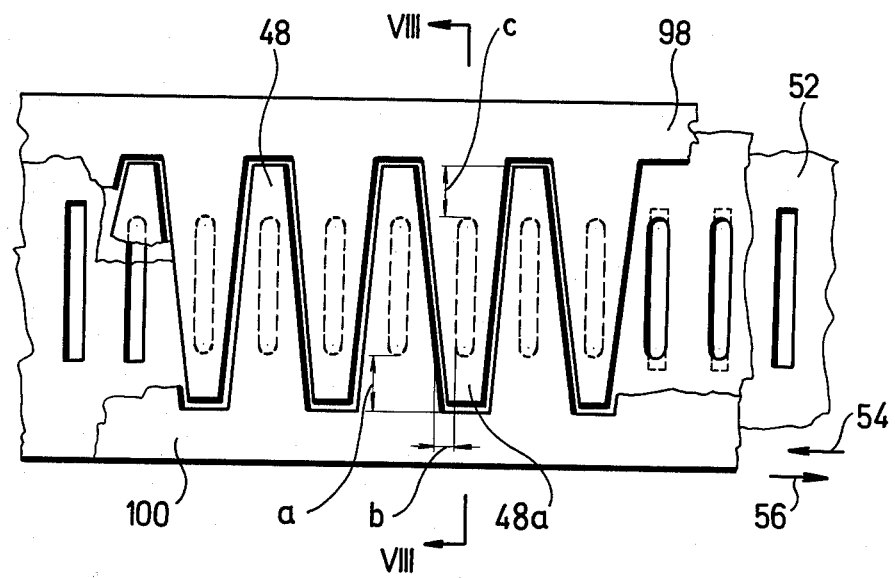
FIG. 7 illustrates a plan view of another exemplified embodiment of the detail shown in FIGS. 5 and 6.

FIGS. 7 and 8 show an exemplified embodiment of a distributor provided with a pair of toothed plates 98 and 100 the teeth of which engage each other in the manner of a toothed joint. It will be apparent from FIG. 8 that by such arrangement of reed fluidization will be more even than with unidirected reeds since the reeds will act symmetrically across the spaces between pairs of sluices 62.

Figure 9:
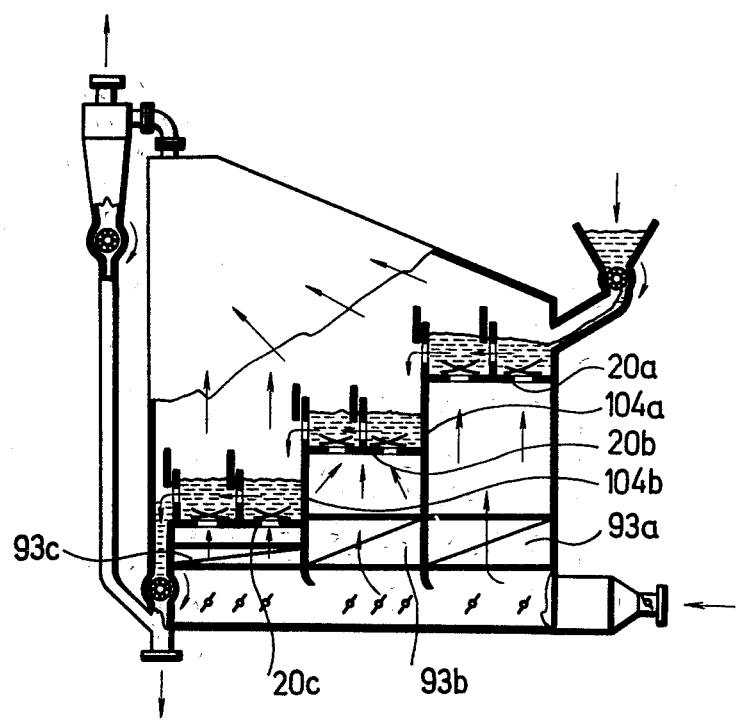
FIG. 9 represents a longitudinal sectional view of a modified embodiment of the apparatus shown in FIGS. 3 and 4.

The exemplified embodiment of the apparatus shown in FIG. 9 differs from the previous one in that it is provided with a plurality of distributors 20a, 20b and 20c of various levels in cascade arrangement between an inlet and an outlet of the type described in connection with the embodiment shown in FIGS. 3 to 6. The distributors 20a, 20b and 20c are separated from one another by partitions 104a and 104b, respectively. It will be seen that the reeds of this exemplified embodiment are of the type shown in FIGS. 7 and 8.

In operation, fluidization may be carried out on the various distributors 20a, 20b and 20c under substantially different operational conditions. It is important that backflow is effectively impeded by the step arrangment of the distributors by which efficiency is considerably increased.

Efficiency of the fluidization method according to the invention will be apparent from the following tables I and II. Table I identifies materials and their characteristics chosen for comparison while table II comprises drying characteristics of the materials set forth in table I, the data being grouped according to the apparatus employed for fluidization.

Table I

Materials and their characteristics

| No. | Material | Average grain size millimeter | Density gram/cubic centimeter | Initial moisture content (H$_2$O + solvent) % |
|---|---|---|---|---|
| 1 | K-asparaginate granular material | 0.68 | 0.71 | 27 |
| 2 | Mg-asparaginate granular material | 1.06 | 0.81 | 8 |
| 3 | phenyl butazone crystalline material | 0.65 | 0.34 | 31 |

Table II

| No. | Material | Type of drier | Drying characteristics | | |
|---|---|---|---|---|---|
| | | | Average operational velocity of air meter/secundum | Heat exploitation Kilogram/steam Kilogram evaporated liquid | Air consumption Cubic meter air/ Kilogram evaporated liquid |
| 1. | K-asparaginate | I | 0.42 | 28.00 | 580.0 |
| | | II | 0.40 | 9.00 | 110.0 |
| | | III | 0.12 | 1.12 | 38.0 |
| 2 | Mg-asparaginate | I | 0.48 | 16.00 | 640.0 |

Table II-continued

| No. | Material | Type of drier | Drying characteristics | | |
|---|---|---|---|---|---|
| | | | Average operational velocity of air meter/secundum | Heat exploitation Kilogram/steam Kilogram evaporated liquid | Air consumption Cubic meter air/ Kilogram evaporated liquid |
| | | II | 0.41 | 10.00 | 190.0 |
| | | III | 0.13 | 1.15 | 50.0 |
| 3. | Phenyl butazone | I | 0.22 | 6.20 | 300.0 |
| | | II | 0.21 | 5.00 | 120.0 |
| | | III | 0.08 | 1.10 | 55.0 |

Type I: Fluidization drying apparatus known per se
Type II: Mixed bed fluidization drier known per se
Type III: Drying apparatus in accordance with the invention.

It will be seen that in case of a method and apparatus according to the invention average operation air velocity, steam and air consumptions amount likewise to a fraction of corresponding parameters of known methods and apparatus, respectively. Distributors as described above might be employed, e.g., multistep and overflow columns where bubble plates consist each of distributors and of reed overlapping orifices thereof as described above. Flow patterns of fluidizing fluid and fluidized bed, respectively, are similar to those shown in FIGS. 1 and 2. The material to be fluidized proceeds from upper levels through overflows onto bubble plates at lower levels. Such arrangement permits to erecting multistage heat and/or mass transfer apparatus of relatively small surface area.

It has been found that beds fluidized in accordance with the present invention are substantially homogeneous. At the same time, operational fluidization velocities are relatively low. Operational gas velocities and gas consumptions are likewise relatively low which means, in addition to energy savings, a simple solvent recovery and permits thereby carrying out sorption operations at relatively low costs.

Obviously, distributors and reeds may be of other than horizontal arrangement. For instance, the distributor might define a curved surface or an oblique plane. The essence is that it should be provided with reeds which overlap the orifices of the distributor whatever its form may be.

What we claim is:

1. A method of fluidizing particulate material, comprising the steps of introducing particulate material to be fluidized into a fluidized bed at one end thereof, passing a fluidizing gas upwardly through the bottom of the bed at a flow velocity by at least one order of magnitude greater than the velocity of fluidization, and causing said fluidizing medium to pass upwardly through the bottom of the bed through orifices that open and close at a frequency that varies inversely as the flow resistance above each individual orifice, and continuously removing the fluidized particulate material at the opposite end of the fluidized bed.

2. A method as claimed in claim 1, and opening and closing said orifices by means of reed valves that are disposed one above each said orifice, said reed valves vibrating between and closed positions at a frequency that varies inversely of the pressure of the fluidized material on the upper side of the valve.

3. Apparatus for fluidizing particulate material, comprising in combination means defining a fluidized bed having a bottom having a plurality of orifices therethrough, means for supplying a fluidizing medium to the bed from below said bottom through said orifices, and reed valves one individual to each said orifice on the upper side of the orifices, said reed valves in their rest positions overlapping said orifices and flexing to open said orifices with a frequency that varies inversely as the local flow resistance prevailing above each said reed valve.

4. Apparatus as claimed in claim 3, said reed valves having the form of teeth of a rake.

5. Apparatus as claimed in claim 3, said reed valves being in the form of interfingering teeth extending in opposite directions from each other.

6. Apparatus as claimed in claim 3, and a displaceable lock plate on the lower side of said bottom, said lock plate having orifices therethrough for selective registration with said orifices through said bottom.

7. Apparatus as claimed in claim 3, and transfer sluices between said ends of said bed.

8. Apparatus as claimed in claim 7, and orifices of variable flow areas through said transverse sluices.

9. Apparatus as claimed in claim 3, and longitudinal baffle plates on the upper side of said bottom defining a reflux passage for a portion of said bed.

10. Apparatus as claimed in claim 3, said bottom being in a plurality of sections at different levels which feed, the higher to the lower, in cascade relationship.

* * * * *